United States Patent
Hsieh

(10) Patent No.: US 8,926,614 B2
(45) Date of Patent: Jan. 6, 2015

(54) MEDICAL ELECTRIC DRILL

(75) Inventor: Chih-Ching Hsieh, Taichung (TW)

(73) Assignee: Kabo Tool Company, Taichung (TW)

(*) Notice: Subject to any disclaimer, the term of this patent is extended or adjusted under 35 U.S.C. 154(b) by 373 days.

(21) Appl. No.: 13/437,943

(22) Filed: Apr. 3, 2012

(65) Prior Publication Data

US 2012/0310247 A1    Dec. 6, 2012

(30) Foreign Application Priority Data

Jun. 3, 2011 (TW) .............................. 100119595 A

(51) Int. Cl.
*A61B 17/00* (2006.01)
*A61B 17/16* (2006.01)
*A61B 19/00* (2006.01)

(52) U.S. Cl.
CPC ... *A61B 17/1626* (2013.01); *A61B 2017/00022* (2013.01); *A61B 2017/00119* (2013.01); *A61B 2019/464* (2013.01); *A61B 2019/466* (2013.01)
USPC .......................................................... 606/80

(58) Field of Classification Search
USPC ......... 606/80; 408/8, 9, 14, 16; 318/432, 434, 318/400.07, 400.14, 400.15, 259, 260, 318/262–263, 270, 271, 779, 799, 721
See application file for complete search history.

(56) References Cited

U.S. PATENT DOCUMENTS

| | | | | |
|---|---|---|---|---|
| 5,745,647 A * | 4/1998 | Krause | .......................... | 388/827 |
| 6,013,991 A * | 1/2000 | Philipp | .......................... | 318/139 |
| 7,022,123 B2 * | 4/2006 | Heldreth | .......................... | 606/80 |
| 7,287,604 B2 * | 10/2007 | Aronstam et al. | .............. | 175/61 |
| 2005/0116673 A1 * | 6/2005 | Carl et al. | ...................... | 318/432 |
| 2005/0131415 A1 * | 6/2005 | Hearn et al. | .................... | 606/80 |
| 2008/0053705 A1 * | 3/2008 | Aronstam et al. | .............. | 175/61 |
| 2010/0125276 A1 * | 5/2010 | Palermo | .......................... | 606/80 |

* cited by examiner

*Primary Examiner* — David Bates
*Assistant Examiner* — Michael Araj
(74) *Attorney, Agent, or Firm* — CKC & Partners Co., Ltd.

(57) ABSTRACT

A medical electric drill includes a drilling head, a microprocessor, a pressure sensor unit, a torque sensor unit and a gravity sensor unit. The drilling head is for drilling a bone. The microprocessor is signally connected to the drilling head for calculating a displacement of the drill. The pressure sensor unit is for detecting a pressure change and provides a pressure change signal to the microprocessor. The torque sensor unit is for detecting a torque change and provides a torque change signal to the microprocessor. The gravity sensor unit is for detecting an acceleration variation of the drilling head and provides an acceleration voltage signal to the microprocessor. The microprocessor determines a work period of drilling the bone according to the pressure change signal and the torque change signal, and then the microprocessor calculates the displacement of the drilling head by using the acceleration voltage signal during the work period.

12 Claims, 2 Drawing Sheets

MEDICAL ELECTRIC DRILL

RELATED APPLICATIONS

The application claims priority to Taiwan Application Serial Number 100119595, filed Jun. 3, 2011, which is herein incorporated by reference.

BACKGROUND

1. Technical Field

The present disclosure relates to a hand-tool device. More particularly, the present disclosure relates to a hand-tool device for medical use.

2. Description of Related Art

With economic development and improvement of material conditions, people are more and more emphasis on the quality of medical care. In addition to the development of research related to medical technology, the design and development of medical devices are also very important issues. Many medical behaviors need the assistance of mechanical tools, especially for surgery operations. For pursuing the safety and accuracy of surgery, the technologies of mechanical automation, precision positioning and so on have been widely used in the development of medical devices.

Among various medical devices, an electric drill is a very common medical hand-tool. For example, when an orthopaedist uses an electric drill to nail a bone nail, the electric drill in general is manually operated and controlled to advance or stop according to the orthopaedist's experience. Besides, if the orthopaedist desires to know the depth of a drilling hole, the orthopaedist needs to withdraw the drill and uses an instrument to measure the drilling hole whether a predetermined depth has been reached. Since the hardness of human bone is varying, an uncertainty of surgical risk exists and surgery time is increased. Moreover, if the orthopaedist controls the drill improperly to make the drilled hole too deep without stopping the drill in time, the patient's body tissues will be harmed greatly.

SUMMARY

According to one embodiment of the present invention, a medical electric drill includes a drilling head, a microprocessor, a pressure sensor unit, a torque sensor unit and a gravity sensor unit. The drilling head is used for drilling a bone. The microprocessor is signally connected to the drilling head for calculating a displacement of the drilling head. The pressure sensor unit is used for detecting a pressure change of the drilling head and providing a pressure change signal to the microprocessor. The torque sensor unit is used for detecting a torque change of the drilling head and providing a torque change signal to the microprocessor. The gravity sensor unit is used for detecting an acceleration variation of the drilling head and providing an acceleration voltage signal to the microprocessor. The microprocessor determines a work period of drilling the bone according to the pressure change signal and the torque change signal, and then the microprocessor calculates the displacement of the drilling head by using the acceleration voltage signal during the work period.

According to another embodiment of the present invention, a medical electric drill includes a drilling head, a microprocessor, a force sensor unit and a gravity sensor unit. The drilling head is used for drilling a bone. The microprocessor is signally connected to the drilling head for calculating a displacement of the drilling head. The force sensor unit is used for detecting a force change of the drilling head and providing a force change signal to the microprocessor. The gravity sensor unit is used for detecting an acceleration variation of the drilling head and providing an acceleration voltage signal to the microprocessor. The microprocessor determines a work period of drilling the bone according to the force change signal, and then the microprocessor calculates the displacement of the drilling hand by using the acceleration voltage signal during the work period.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
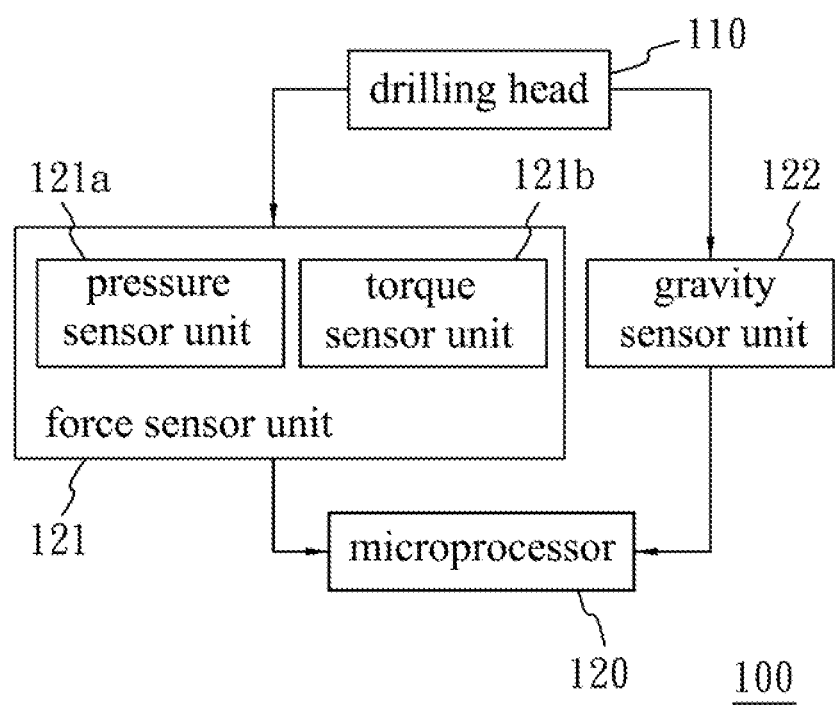
FIG. 1 is a functional block diagram showing a medical electric drill according to one embodiment of the present invention.

FIG. 1 is a functional block diagram showing a medical electric drill according to one embodiment of the present invention. As shown in FIG. 1, a medical electric drill 100 includes a drilling head 110, a microprocessor 120, a force sensor unit 121 and a gravity sensor unit 122. The present embodiment uses the special designed microprocessor 120 to control a depth of a drilling hole formed by the drilling head 110.

The drilling head 110 is used for drilling a bone. The microprocessor 120 is signally connected to the drilling head 110 for calculating a displacement of the drilling head 110.

The force sensor unit 121 has many options. In the present embodiment, a pressure sensor unit 121a and a torque sensor unit 121b are used as the force sensor unit 121. The pressure sensor unit 121a is used for detecting a pressure change of the drilling head 110 and providing a pressure change signal to the microprocessor 120. The torque sensor unit 121b is used for detecting a torque change of the drilling head 110 and providing a torque change signal to the microprocessor 120. The gravity sensor unit 122 is used for detecting an acceleration variation of the drilling head 110 and providing an acceleration voltage signal to the microprocessor 120.

It is worthy to be noted that the microprocessor 120 determines a work period of drilling the bone according to the pressure change signal and the torque change signal, that is, the microprocessor 120 determines a start time and an end time of the drilling head 110 to drill the bone. Then, the microprocessor 120 defines a work period in accordance with duration of the start time and the end time. After defining the work period, the microprocessor 120 calculates the displacement of the drilling hand 110 in accordance with the acceleration voltage signal during the work period.

Moreover, the gravity sensor unit 122 of the present embodiment is a three-axis gravity sensor unit for controlling a displacement direction of the drilling head. In other words, the gravity sensor unit 122 can both control the displacement direction and angle of the drilling head 110 during the moving of the drilling head 110, thereby preventing the drilling head 110 from departing from a predetermined direction and a predetermined angle when the drilling since is hand held by a user.

Figure 2:
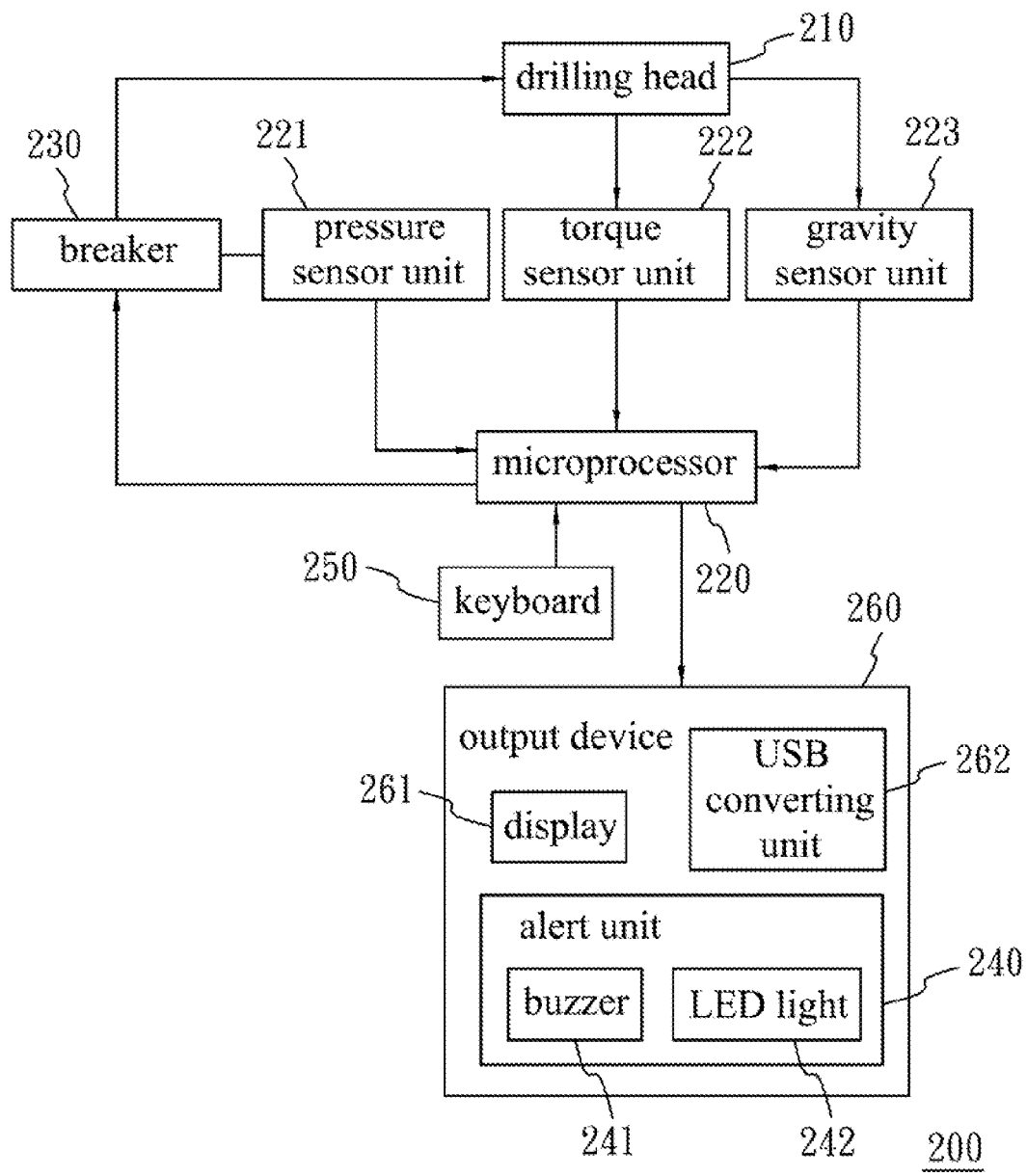
FIG. 2 is a functional block diagram showing a medical electric drill according to another embodiment of the present invention.

FIG. 2 is a functional block diagram showing a medical electric drill according to another embodiment of the present invention. As shown in FIG. 2, the medical electric drill 200 of the present embodiment is similar to the medical electric drill 100 of the above embodiment. The difference there between is that the present embodiment has a breaker 230 and an alert unit 240 in addition to the aforementioned components.

The breaker 230 can be connected to the pressure sensor unit 221, the torque sensor unit 222, or the gravity sensor unit 223. In the present embodiment, the breaker 230 is connected to the pressure sensor unit 221 for stopping the drilling head 210 from being rotated when the pressure change of the drilling head 210 detected by the pressure sensor unit 221 reaches a predetermined pressure value. Taking a human bone as an example, since the density and hardness of an outer layer of a human bone is greater than those of an inner layer thereof. When the drilling head 110 drills through the outer layer of the human bone at the first time, the pressure of the drilling head 110 will decrease since the drilling head 110 enters the inner layer of the human bone. Meanwhile, the pressure sensor unit 221 will also detect that the pressure change of the drilling head 210 reaches a predetermined pressure value. In other to prevent the drilling head 210 from drilling through the outer layer of the human bone at the second time, meaning the human bone is on the verge of being drilled through, the microprocessor 220 should stop the rotation of the drilling head 210.

If the breaker 230 is connected to the torque sensor unit 222, the breaker 230 stops the drilling head 210 from being rotated when the torque change of the drilling head 210 detected by the torque sensor unit 222 reaches a predetermined torque value. On the other hand, if the breaker 230 is connected to the gravity sensor unit 223, the breaker 230 stops the drilling head 210 from being rotated when the displacement of the drilling head 210 detected by the gravity sensor unit 223 reaches a predetermined displacement value, wherein an input device, such as a keyboard 250, can be disposed for inputting the predetermined displacement value into the microprocessor 220, and then an output device 260 is used to display the present displacement value on a display 261 or on a computer display via a USB converting unit 262, thereby allowing the user to learn the present displacement value promptly for reducing the probability of drilling errors.

The alert unit 240 is used for issuing an alert signal when the breaker 230 is activated. For instance, the breaker 230 of the present embodiment is connected to the pressure sensor unit 221, and thus the breaker 230 will be activated when the pressure change of the drilling head 210 detected by the pressure sensor unit 221 reaches a predetermined pressure value, and then the alert unit 240 will issue sound or light to warn the user. The alert unit 240 can be a buzzer 241, a LED light 242, etc.

Specifically, the medical electric drill 200 of the present embodiment uses the pressure sensor unit 221 to detect the pressure of the drilling head 210. When the pressure change of the drilling head 210 detected by the pressure sensor unit 221 reaches a predetermined pressure value, the breaker 230 is activated and the pressure sensor unit 221 provides a pressure, change signal to the microprocessor 220 and this time point is noted as a start time. Moreover, the three-axis gravity sensor unit controls the displacement direction to and angle of the drilling head 210 during the drilling. On the other hand, the torque sensor unit 222 continually detects the torque change of the drilling head 210. When the torque change of the drilling head 210 reaches a predetermined torque value, the breaker 230 will stop the drilling head 210 from being rotated and this time point is noted as an end time by the microprocessor 220. Thereafter, the microprocessor 220 provides a work period according to the start time and the end time, and the gravity sensor unit 223 provides an acceleration voltage signal to the microprocessor 220 during the work period. Finally, the microprocessor 220 computes the displacement of the drilling hand 110 by using the acceleration voltage signal provided by the gravity sensor unit 223.

According to the aforementioned embodiments, the medical electric drill of the present embodiment not only controls the depth of the drilling by the pressure sensor unit 221, the torque sensor unit 222 and the gravity sensor unit 223, but also improves the accuracy of drilling direction and drilling angle by the three-axis gravity sensor unit. In addition, the devices such as the breaker and the alert unit can effectively control the progress and timing of surgery, and also indeed provide a simple and accurate device for the current surgery.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A medical electric drill, comprising:
a drilling head for drilling a bone;
a microprocessor which is connected to the drilling head for calculating a displacement of the drilling head;
a pressure sensor unit for detecting a pressure change of the drilling head and providing a pressure change signal to the microprocessor;
a torque sensor unit for detecting a torque change of the drilling head and providing a torque change signal to the microprocessor; and
a gravity sensor unit for detecting an acceleration variation of the drilling head and providing an acceleration voltage signal to the microprocessor;
wherein the microprocessor determines a work period of drilling the bone according to the pressure change signal provided by the pressure sensor unit and the torque change signal provided by the torque sensor unit, and then the microprocessor calculates the displacement of the drilling head by using the acceleration voltage signal during the work period;
wherein the work period is a duration between a start time and an end time of the drilling head drilling the bone.

2. The medical electric drill of claim 1, further comprising:
a breaker for stopping the drilling head from being rotated when the pressure change of the drilling head detected by the pressure sensor unit reaches a predetermined pressure value.

3. The medical electric drill of claim 2, further comprising:
an alert unit issuing an alert signal when the breaker is activated.

4. The medical electric drill of claim 1, further comprising:
a breaker for stopping the drilling head from being rotated when the torque change of the drilling head detected by the torque sensor unit reaches a predetermined torque value.

5. The medical electric drill of claim 4, further comprising:
an alert unit issuing an alert signal when the breaker is activated.

6. The medical electric drill of claim 1, further comprising:
a breaker for stopping the drilling head from being rotated when the displacement of the drilling head detected by the gravity sensor unit reaches a predetermined displacement value.

7. The medical electric drill of claim 6, further comprising:
an alert unit issuing an alert signal when the breaker is activated.

8. The medical electric drill of claim 1, wherein the gravity sensor unit is a three-axis gravity sensor unit for controlling a displacement direction of the drilling head.

9. A medical electric drill, comprising:
a drilling head for drilling a bone;
a microprocessor which is connected to the drilling head for calculating a displacement of the drilling head;
a force sensor unit for detecting a force change of the drilling head and providing a force change signal to the microprocessor; and
a gravity sensor unit for detecting an acceleration variation of the drilling head and providing an acceleration voltage signal to the microprocessor;
wherein the microprocessor determines a work period of drilling the bone according to the force change signal provided by the force sensor unit, and then the microprocessor calculates the displacement of the drilling head by using the acceleration voltage signal during the work period;
wherein the work period is a duration between start time and an end time of the drilling head drilling the bone.

10. The medical electric drill of claim 9, further comprising:
a breaker for stopping the drilling head from being rotated when the displacement of the drilling head detected by the gravity sensor unit reaches a predetermined displacement value.

11. The medical electric drill of claim 9, wherein the force sensor unit is a pressure sensor unit.

12. The medical electric drill of claim 9, wherein the force sensor unit is a torque sensor unit.

* * * * *